US005962665A

United States Patent [19]
Kroeger et al.

[11] Patent Number: 5,962,665
[45] Date of Patent: Oct. 5, 1999

[54] NUCLEIC ACID PRIMERS AND PROBES FOR DETECTING HIV-1 AND HIV-2

[75] Inventors: Paul E. Kroeger, Lindenhurst; Klara Abravaya, Wilmette; Claudia A. Cygan Esping, Geneva; Jacek J. Gorzowski, Round Lake Park; Robert J. Hoenle, Crystal Lake; Jennifer J. Moore, Chicago, all of Ill.

[73] Assignee: Abbott Laboratories, Abbott Park, Ill.

[21] Appl. No.: 08/876,546

[22] Filed: Jun. 16, 1997

[51] Int. Cl.⁶ .......................... C07H 21/02; C07H 21/04; C12Q 1/68; C12Q 1/70
[52] U.S. Cl. .......................... 536/23.1; 536/24.3; 435/6; 435/5
[58] Field of Search .................. 536/23.1, 24.3; 435/6, 5; 935/76, 77, 78

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,965,188 | 10/1990 | Mullis et al. . |
| 5,306,614 | 4/1994 | Alizon et al. ............... 435/5 |
| 5,310,651 | 5/1994 | Alizon et al. ............... 435/6 |
| 5,569,582 | 10/1996 | Tavernarakis et al. . |
| 5,578,715 | 11/1996 | Alizon et al. . |
| 5,587,468 | 12/1996 | Allen et al. . |
| 5,594,123 | 1/1997 | Sninsky et al. ............ 536/24.32 |
| 5,599,662 | 2/1997 | Respess ..................... 435/5 |
| 5,629,153 | 5/1997 | Urdea . |
| 5,637,455 | 6/1997 | Henco et al. ............... 435/5 |
| 5,688,637 | 11/1997 | Moncany et al. ........... 435/6 |

FOREIGN PATENT DOCUMENTS

| | | |
|---|---|---|
| 0181150 | 5/1986 | European Pat. Off. . |
| 0239425 | 11/1989 | European Pat. Off. . |
| 0404625 | 12/1990 | European Pat. Off. . |
| 0617132 | 9/1994 | European Pat. Off. . |
| 07 27497 | 8/1996 | European Pat. Off. . |
| 0731175 | 9/1996 | European Pat. Off. . |
| 0504278 | 1/1997 | European Pat. Off. . |
| 0516540 | 1/1997 | European Pat. Off. . |
| 2652091 | 3/1991 | France . |
| 9110746 | 7/1991 | WIPO . |
| WO9216180 | 10/1992 | WIPO . |
| 9313223 | 7/1993 | WIPO . |
| 9403635 | 2/1994 | WIPO . |
| 9514109 | 5/1995 | WIPO . |
| 9602557 | 2/1996 | WIPO . |
| 9707235 | 2/1997 | WIPO . |

OTHER PUBLICATIONS

Kellogg et al., in "PCR Protocols: A Guide to Methods and Applications," pp. 337–347, Academic Press, Inc., San Diego, CA (1990).
Montpetit et al., J. of Virological Methods 36: 119–128 (1992).
Bootman et al., J. of Virological Methods 37 : 23–42 (1992).
Hunt et al., Leukemia 11 Suppl. 3 : 138–141 (Apr. 1997).
Zagury et al., PNAS 85 : 5941–5945 (1988).
The Stratagene Catalog, p. 39 (1988 Edition).
Udaykumar et al., J. of Virological Methods 49 :47–46(1994).
Abravaya, K., et al., "Research Investigations into the Suitability of the LCx® Platform for Detection of Bloodborne Viruses", *Infusionsather Transfusionsmed*, 25:170–177 (1998).
Brown, V., et al., "Detection of HIV–1 and 2 infection by the polymerase chain reaction PCR", *Abstract of the Gen. Mtg of the Amer. Soc. For Microbiology*, 91(0):335 (1991).
Carman, W. F., et al., "Detection of Enzymatically Amplified Human Immunodeficiency Virus DNA by Oligonucleotide Solution Hybridization and by Incorporation of Radiolabeled Deoxynucleotides", *Journof Clinical Microbiology*, 27(11):2570–2573.
Gingeras, T. R., et al., "Use of Self–Sustained Sequence Replication Amplification Reaction to Analyze and Detect Mutations in Zidovudine–Resistant Human Immunodeficiency Virus", *The Journ of Infectious Diseases*, 164(6):1066–1074 (1991).
Respess, R. A., et al., "Detection of Genetically Diverse Human Immunodeficiency Virus Type 1 Group M and O Isolates by PCR", *Journ of Clinical Microbiology*, 35(5):1284–1286 (1997).

*Primary Examiner*—W. Gary Jones
*Assistant Examiner*—Ethan Whisenant
*Attorney, Agent, or Firm*—Paul D. Yasger

[57] ABSTRACT

Provided herein are primer/probe sets useful for detecting HIV (i.e. either or both HIV 1 or HIV 2) in a test sample. The primer/probe sets are can be employed according to nucleic acid amplification procedures including PCR or RT PCR. The primer/probe sets can also be provided in the form of a kit with other reagents for performing a nucleic acid amplification reaction.

9 Claims, No Drawings

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 2348 bases
      (B) TYPE: nucleic acid
      (C) STRANDEDNESS: single
      (D) TOPOLOGY: linear (ii) MOLECULE TYPE: genomic RNA (HIV-1)

(xi) SEQUENCE DESCRIPTION: SEQ ID NO:1:

```
ACAGTATTAG TAGGACCTAC ACCTGTCAAC ATAATTGGAA GAAATCTGTT           50

GACTCAGCTT GGGTGCACTT TAAATTTTCC CATTAGTCCT ATTGAAACTG          100

TACCAGTAAA ATTAAAGCCA GGAATGGATG GCCCAAAAGT TAAACAATGG          150

CCATTGACAG AAGAAAAAAT AAAAGCATTA ATAGAAATTT GTACAGAAAT          200

GGAAAAGGAA GGGAAAATTT CAAAAATTGG GCCTGAAAAT CCATACAATA          250

CTCCAGTATT TGCCATAAAG AAAAAAGACA GTACTAAATG GAGAAAATTA          300

GTAGATTTCA GAGAACTTAA TAAGAAAACT CAAGACTTCT GGGAAGTTCA          350

ATTAGGAATA CCACATCCTG CAGGGTTAAA AAAGAAAAAA TCAGTAACAG          400

TACTGGATGT GGGTGATGCA TATTTTTCAG TTCCCTTAGA TAAAGACTTC          450

AGGAAGTATA CTGCATTTAC CATACCTAGT ATAAACAATG AAACACCAGG          500

GATTAGATAT CAGTACAATG TGCTTCCACA GGGATGGAAA GGATCACCAG          550
```

-continued

| | |
|---|---|
| CAATATTCCA AAGTAGCATG ACAAAAATCT TAGAGCCTTT TAGAAAACAA | 600 |
| AATCCAGACA TAGTTATCTA TCAATACATG GATGATTTGT ATGTAGGATC | 650 |
| TGACTTAGAA ATAGGGCAGC ATAGAGCAAA AATAGAGGAA CTGAGACGAC | 700 |
| ATCTGTTGAG GTGGGGATTT ACCACACCAG ACAAAAAACA TCAGAAAGAA | 750 |
| CCTCCATTCC TTTGGATGGG TTATGAACTC CATCCTGATA AATGGACAGT | 800 |
| ACAGCCTATA GTGCTACCAG AAAAAGACAG CTGGACTGTC AATGACATAC | 850 |
| AGAAGTTAGT GGGAAAATTG AATTGGGCAA GTCAGATTTA CGCAGGGATT | 900 |
| AAAGTAAAGC AATTATGTAA ACTCCTTAGA GGAACCAAAG CACTAACAGA | 950 |
| AGTAATACCA CTAACAGAAG AAGCAGAGCT AGAACTGGCA GAAAACAGGG | 1000 |
| AAATTCTAAA AGAACCAGTA CATGGAGTGT ATTATGACCC ATCAAAAGAC | 1050 |
| TTAATAGCAG AAGTACAGAA GCAGGGGCAA GGCCAATGGA CATATCAAAT | 1100 |
| TTATCAAGAG CCATTTAAAA ATCTGAAAAC AGGCAAATAT GCAAGAATGA | 1150 |
| GGGGTGCCCA CACTAATGAT GTAAAACAAT TAACAGAGGC AGTGCAAAAA | 1200 |
| ATAGCCACAG AAAGCATAGT AATATGGGGA AAGACTCCTA AATTTAGACT | 1250 |
| ACCCATACAA AAAGAAACAT GGGAAACATG GTGGACAGAG TATACGTAAG | 1300 |
| CCACCTGGAT TCCTGAGTGG GAGGTTGTCA ATACCCCTCC CTTAGTGAAA | 1350 |
| TTATGGTACC AGTTAGAGAA AGAACCCATA GTAGGTGCAG AAACTTTCTA | 1400 |
| TGTAGATGGG GCAGCTAACA GGGAGACTAA AAAAGGAAAA GCAGGATATG | 1450 |
| TTACTAACAG AGGAAGACAA AAGGTTGTCT CCCTAACTGA CACAACAAAT | 1500 |
| CAGAAGACTG AGTTACAAGC AATTCATCTA GCTTTGCAAG ATTCAGGGTT | 1550 |
| AGAAGTAAAC ATAGTAACAG ACTCACAATA TGCATTAGGA ATCATTCAAG | 1600 |
| CACAACCAGA TAAAAGTGAA TCAGAGTTAG TCAGTCAAAT AATAGAGCAG | 1650 |
| TTAATAAAAA AGGAAAAGGT CTATCTGGCA TGGGTACCAG CACACAAAGG | 1700 |
| AATTGGAGGA AATGAACAAG TAGATAAATT AGTCAGTGCT GGAATCAGGA | 1750 |
| AAGTACTATT TTTAGATGGA ATAGATAAGG CCCAAGAAGA CCATGAGAAA | 1800 |
| TATCACAGTA ATTGGAGAGC AATGGCTAGT GACTTTAACC TACCACCTAT | 1850 |
| AGTAGCAAAA GAAATAGTAG CCAGCTGTGA TAAATGTCAG CTAAAAGGAG | 1900 |
| AAGCCATGCA TGGACAAGTA GACTGTAGTC CAGGAATATG GCAACTAGAT | 1950 |
| TGTACACATT TAGAAGGAAA AGTTATCCTG GTAGCAGTTC ATGTAGCCAG | 2000 |
| TGGATACATA GAAGCAGAAG TTATTCCAGC AGAGACAGGG CAGGAGACAG | 2050 |
| CATACTTTCT CTTAAAATTA GCAGGAAGAT GGCCAGTAAA AACAATACAT | 2100 |
| ACAGACAATG GCCCCAATTT CACCAGTACT ACGGTTAAGG CCGCCTGTTG | 2150 |
| GTGGACGGGA ATCAAGCAGG AATTTGGCAT TCCCTACAAT CCCCAAAGTC | 2200 |
| AAGGAGTAAT AGAATCTATG AATAAAGAAT TAAAGAAAAT TATAGGACAG | 2250 |
| GTAAGAGATC AGGCTGAACA TCTTAAGAGA GCAGTACAAA TGGCAGTATT | 2300 |
| CATCCACAAT TTTAAAAGAA AAGGGGGGAT TGGGGGGTAC AGTGCAGG | 2348 |

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:2:

ATTCCCTACA ATCCCCAAAG TCAAGGAGT 29

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:3:

CCTGCACTGT ACCCCCCAAT CC 22

(2) INFORMATION FOR SEQ ID NO: 4:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO: 4:

ACAGCAGTAC AAATGGCA 18

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

GGAGCAGAAA CTTTCTATGT AGATGG 26

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

CATATTGTGA GTCTGTTACT ATGTTTACT 29

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

TAGGAAAAGC AGGATATG                                                         18

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:8:

GGTACAGTAT TAGTAGGACC TACACCTGT                                             29

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:9:

GGCCATTGTT TAACTTTTGG GCCATCCA                                              28

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:10:

ATTAGTCCTA TTGAAACTGT                                                       20

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:11:

ATAAGCCCCA TAGCC                                                            15

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:12:

CCTAGTATAA ACAATGAGAC ACCAGG                                                26

(2) INFORMATION FOR SEQ ID NO:13:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:13:

GATCCTACAT ACAAGTCATC CATGTA                                              26

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:14:

GGATGGAAAG GATCACCA                                                       18

(2) INFORMATION FOR SEQ ID NO:15:

(i) SEQUENCE CHARACTERISTICS:
            (A) LENGTH: 2689 base pairs
            (B) TYPE: nucleic acid
            (C) STRANDEDNESS: single
            (D) TOPOLOGY: linear (ii) MOLECULE TYPE: genomic RNA (HIV-2)

(xi) SEQUENCE DESCRIPTION: SEQ ID NO:15:

TTGCTGCACC TCAATTCTCT CTTTGGAAAA GACCAGTAGT CACAGCACAC                    50

ATTGAGGGTC AGCCAGTAGA AGTTTTGTTA GACACAAGGG CTAACGACTC                   100

AATAGTAGCA GGAATAGAGT TAGGGAGCAA TTATAGTCCA AAAATAGTAG                   150

GAGGAATAGG GGGATTCATA AATACCAAGG AATATAAAAA TGTAGAAATA                   200

GAAGTCCTAG GTAAAAGGGT AAAAGCCACC ATAATGACAG GTGATACCCC                   250

GATCAACATT TTTGGCAGAA ATGTTCTGAC AGCTTTAGGC ATGTCATTAA                   300

ACCTGCCAGT TGCCAAGATA GAACCAATAA AAATAATGCT AAAGCCAGGG                   350

AAAGATGGAC CAAGACTAAA ACAATGGCCT TTAACAAAAG AAAAAATAGA                   400

AGCACTAAAA GAAATCTGTG AAAAAATGGA AAAAGAAGGC CAGCTAGAAG                   450

AAGCACCTCC AACTAATCCT TATAATACCC CCACATTTGC AATCAAGAAA                   500

AAGGACAAAA ACAAATGGAG AATGCTAATA GACTTTAGGG AGCTAAACAA                   550

GGTAACTCAG GATTTCACAG AAATTCAGTT AGGAATTCCA CACCCAGCAG                   600

GATTGGCCAA AAGAGGAGA ATTACTGTAC TAGATGTAGG GGATGCTTAC                    650

TTTTCCATAC CACTACATGA GGACTTTAGA CAGTATACTG CATTCACTCT                   700

ACCATCAGTA AACAATGCAG AACCAGGAAA AAGATATATA TACAAAGTCC                   750

TACCACAGGG GTGGAAGGGG TCACCAGCAA TTTTTCAATA CACAATGAGG                   800

CAGATCTTAG AACCATTCAG AAAAGCAAAC GAGGATGTCA TTATCATTCA                   850

GTACATGGAT GATATCTTAA TAGCCAGCGA CAGGACAGAC TTAGAACATG                   900

ACAAAGTGGT CCTGCAGCTA AAAGAACTTC TAAATGGACT AGGATTTTCC                   950

ACCCCAGATG AGAAATTCCA GAAAGACCCT CCATATCGCT GGATGGGCTA                  1000

```
TGAATTATGG CCAACTAAAT GGAAGTTGCA AAAAATACAG CTGCCCCAAA        1050

AAGAAGTATG GACAGTCAAT GACATCCAAA AGCTAGTGGG TGTCCTAAAT        1100

TGGGCAGCAC AAATCTACCC AGGGATAAAG ACCAAACACC TATGTAGGCT        1150

AATTAGAGGA AAAATGACAC TCACAGAAGA GGTACAGTGG ACAGAATTAG        1200

CAGAAGCAGA GCTAGAGGAA AACAGAATTA TCTTAAGCCA GAAACAAGAA        1250

GGACACTATT ACCAGGAAGA AAAAAGTTA GAAGCAACAG TCCAGAAAGA         1300

TCAAGACAAT CAGTGGACAT ATAAGGTACA CCAGGGGGAA AAAATTCTCA        1350

AAGGTGGGAA AATATGCAAA GATAAAAAAT ACCCATACCA ACGGGTCAGA        1400

TTGTTAGCAC AGGTAGTTCA AAAAATAGGA AAAGAAGCAC TAGTCATTTG        1450

GGGACGGATA CCAAAATTTC ACCTACCAGT AGAGAGAGAT ACCTGGGAGC        1500

AGTGGTGGGA TAACTACTGG CAAGTAACAT GGATCCCAGA CTGGGACTTT       1550

GTATCTACCC CACCACTGGT CAGGCTAGCA TTTAACCTGG TAGGAGAGCC        1600

TGTACCAGGC GCAGAAACTT TCTACACAGA TGGATCCTGC AATAGGCAGT       1650

CAAAAGAAGG GAAAGCAGGA TATATAACAG ATAGAGGGAG AGACAGGGTA        1700

AAAGTATTAG AGCAAACTAC CAATCAGCAA GCAGAATTAG AAGCCTTTGC        1750

AATGGCACTA ACAGACTCAG GTCCAAAAGC TAATATTATA GTAGACTCAC        1800

AATATGTAAT GGGGATAGTA GCAGGCCAAC CAACAGAGTC AGAGAATAGA        1850

ATAGTAAATC AGATCATAGA AGAAATGATA AGAAAGAAG CAATCTATGT         1900

TGCGTGGGTC CCAGCCCACA AAGGCATAGG AGGAAACCAG GAAGTAGATC        1950

ATTTAGTAAG TCAGGGCATT AGACAAGTAT TATTCCTAGA GAAATAGAA         2000

CCCGCGCAGG AAGAACATGA AAAATATCAT AGCAATATAA AAGAACTGTC        2050

CCATAAATTT GGAATACCCA AGCTAGTGGC AAGACAAATA GTAAACACAT        2100

GTGCCCATGT GCAACAGAAA GGGGAGGCTA TACATGGGCA AGTAAATGCA        2150

GAACTAGGCA CTTGGCAAAT GGACTGCACA CATTTAGAAG GAAAAGTCAT        2200

TATAGTAGCA GTACATGTTG CAAGTGGATT TATAGAGGCA GAAGTTATCC        2250

CACAGGAATC AGGAAGGCAA ACAGCACTGT TCTTACTGAA ACTGGCCAGT        2300

AGGTGGCCAA TAACACACCT GCACACAGAT AATGGTGCCA ACTTCACTTC        2350

ACAGGAAGTG AAAATGGTAG CATGGTGGGT AGGTATAGAA CAAACCTTTG        2400

GAGTGCCTTA CAATCCACAA AGCCAAGGAG TAGTAGAAGC AATGAATCAT        2450

CATCTAAAAA ATCAGATAGA CAGAATTAGA GAGCAGGCAA ATACAGTAGA        2500

AACAATAGTA TTAATGGCAG TTCATTGCAT GAATTTTAAA AGAAGGGGAG        2550

GAATAGGGGA TATGACCCCA GCAGAAAGAA TAATCAATAT GATCACCACA        2600

GAACAAGAAA TACAATTCCT CCAAGCAAAA AATTCAAAAT TAAAAAATTT        2650

TCGGGTCTAT TTCAGAGAAG GCAGAGATCA GCTGTGGAA                   2689
```

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:16:

ACTGATGGCA GTTCATTGCA TGAATTTTAA AAG                           33

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:17:

TTCCACAGCT GATCTCTGCC TTCTCTG                                  27

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:18:

CAGAACAAGA AATACAATTC                                          20

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:19:

CCTCAATTCT CTCTTTGGAA AAGACC                                   26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:20:

AAATGTTGAT TGGGGTATCT CCTGTC                                   26

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:21:

CCAAAAATAG TAGGGGG                                             17

(2) INFORMATION FOR SEQ ID NO:22:

```
(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:22:

ATAGTAGCAG GAATAGA                                                17

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:23:

CAATAGTAGC AGGAATAGAG TTAGG                                       25

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:24:

CACAGCTGAT CTCTGCCTTC TCTGTAATAG AC                               32
```

NUCLEIC ACID PRIMERS AND PROBES FOR DETECTING HIV-1 AND HIV-2

FIELD OF THE INVENTION

The present invention relates to HIV. In particular the—invention relates to oligonucleotides and methods for detecting HIV 1 and HIV 2.

BACKGROUND OF THE INVENTION

Viruses classified as HIV contain RNA as their genetic information and the infectivity of HIV depends upon the virus's ability to insert its genetic information into the DNA of a host. In order to insert its genetic information and therefore successfully infect a host, an HIV virus must convert its genetic material (RNA) into DNA so that the HIV genetic information is compatible with that of the host. Apparently, HIV is successful at converting its RNA into DNA, given the prevalence of AIDS. However, while the virus may successfully convert RNA into DNA, the conversion is seldom accurate. In other words, the DNA copy of the viral RNA is ndtmethods exact and the DNA copy can diverge from the viral RNA by several base pairs. Hence, while a host initially may be infected with a single virus particle, after several rounds of replication, the host may be infected with a genetically diverse population of viruses.

Although HIV is not uniformly classified, it is generally accepted that HIV 1 and HIV2 are different viruses. Within each of these viral classifications are several groups or subtypes. For example, within the classification HIV 1, there is "group M", which is further classified into subtypes A–F, and "group O". HIV 2, on the other hand, contains subtypes A–E. Subtypes of HIV 1 and HIV 2 are broken down even further into categories to numerous to mention in this context. However, it is worth mentioning that all of these divisions are based upon the genetic variance between the viruses and, according to taxonomic theory, many of these viruses are the progeny of a single virus. Hence, the numerous HIV types and subtypes demonstrate the highly mutable nature of HIV and the genetic variability of the HIV genome.

The genetic variability of the virus can be attributed to the inefficiency with which the virus converts its RNA into DNA, as mentioned above. Another theory concerning the genetic variability of the virus is that hosts can be infected with multiple different populations of HIV (which as mentioned above, can arise out of an infection by a single virus) and through the course of replication and packaging of the viral genetic information, pieces of one viral genome can be recombined with pieces of another viral genome. Hence, upon packaging of the recombined genome, a genetically distinct virus is formed. Regardless of the manner by which the virus mutates, it is clear that viruses known as HIV have genomes that are highly mutable and are therefore constantly changing. This presents those searching for methods of detecting the virus based upon its genetic information with a constantly moving target.

Although it is known that certain regions of the HIV genome are conserved, this is not to say that these regions are immune from mutation particularly if mutations in these regions do not effect the structure of a protein encoded by these regions. Hence, developing reagents and methods for detecting HIV based upon its genetic information is a continuing challenge.

SUMMARY OF THE INVENTION

The present invention provides reagents useful for detecting HIV (that is the various subtypes of HIV 1 and HIV 2) based upon the genetic information of these viruses. In particular, the reagents are in the form of primer and probe sets which can be employed according to nucleic acid amplification procedures to specifically and sensitively detect various subtypes of HIV 1 and HIV 2. Preferably, the primer/probe sets herein provided comprise two primer sequences and one probe sequence and are employed according to a reverse transcriptase (RT) PCR format.

Primer/probe sets of the invention which can be employed to detect HIV 1 are designated herein as primer/probe set 1 (SEQ. ID. NOs. 2, 3 and 4); primer/probe set 2 (SEQ. ID. NOs. 5, 6 and 7); primer/probe set 3 (SEQ. ID. NOs. 8, 9, 10 and 11); and primer/probe set 4 (SEQ. ID. NOs. 12, 13 and 14). Primer/probe sets which can be employed to detect HIV 2 are designated herein as primer/probe set 5 (SEQ. ID. NOs. 16, 17 and 18); primer/probe set 6 (SEQ. ID. NOs. 19, 20 and 21 or 22); primer/probe set 7 (SEQ. ID. NOs. 23, 20 and 21); and primer/probe set 8 (SEQ. ID. NOs. 16, 24 and 18).

The method for detecting HIV will generally comprise the steps of (a) forming a reaction mixture comprising nucleic acid amplification reagents, at least one primer/probe set mentioned above, and a test sample containing an HIV target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of HIV in the test sample.

The preferred RT PCR format will comprise the same steps as mentioned above but the amplification reagents will comprise an enzyme having reverse transcriptase activity. In addition, according to any of the methods provided herein, step (b) can be repeated multiple times to increase the number of target sequence copies. It will be understood by those skilled in the art that step (b) can be repeated through thermal cycling the reaction mixture.

DETAILED DESCRIPTION OF THE INVENTION

The primer/probe sets provided herein comprise two primers and at least one probe. These primer/probe sets can be employed according to nucleic acid amplification techniques. Hence, the primers in any particular primer/probe set can be employed to amplify a target sequence. In most cases, the probe hybridizes to the copies of the target sequence generated by one of the primers and generally facilitates detecting any copies of the target sequence generated during the course of the amplification reaction. All of the primer/probe sets can be employed according to nucleic acid amplification procedures to specifically and sensitively detect HIV 1 group M and group O, as well as the various subtypes of HIV 2. Primer/probe sets for detecting HIV 1 subtypes are presented below in Table 1 and primer/probe sets for detecting HIV 2 subtypes are presented in Table 2 below.

TABLE 1

| Primer/Probe Set | Sequence (5'-3') | SEQ. ID. NO. |
|---|---|---|
| 1 | ATTCCCTACAATCCCCAAAGTCAAGGAGT | 2 |
| | CCTGCACTGTACCCCCCAATCC | 3 |
| | ACAGCAGTACAAATGGCA | 4 |
| 2 | GGAGCAGAAACTTTCTATGTAGATGG | 5 |
| | CATATTGTGAGTCTGTTACTATGTTTACT | 6 |
| | TAGGAAAAGCAGGATATG | 7 |

TABLE 1-continued

| Primer/Probe Set | Sequence (5'-3') | SEQ. ID. NO. |
|---|---|---|
| 3 | GGTACAGTATTAGTAGGACCTACACCTGT | 8 |
|   | GGCCATTGTTTAACTTTTGGGCCATCCA | 9 |
|   | ATTAGTCCTATTGAAACTGT | 10 |
|   | ATAAGCCCCATAGCC | 11 |
| 4 | CCTAGTATAAACAATGAGACACCAGG | 12 |
|   | GATCCTACATACAAGTCATCCATGTA | 13 |
|   | GGATGGAAAGGATCACCA | 14 |

TABLE 2

| Primer/Probe Set | Sequence (5'-3') | SEQ. ID. NO. |
|---|---|---|
| 5 | ACTGATGGCAGTTCATTGCATGAATTTTAAAAG | 16 |
|   | TTCCACAGCTGATCTCTGCCTTCTCTG | 17 |
|   | CAGAACAAGAAATACAATTC | 18 |
| 6 | CCTCAATTCTCTCTTTGGAAAAGACC | 19 |
|   | AAATGTTGATTGGGGTATCTCCTGTC | 20 |
|   | CCAAAAATAGTAGGGGG | 21 |
|   | ATAGTAGCAGGAATAGA | 22 |
| 7 | CAATAGTAGCAGGAATAGAGTTAGG | 23 |
|   | AAATGTTGATTGGGGTATCTCCTGTC | 20 |
|   | CCAAAAATAGTAGGGGG | 21 |
| 8 | ACTGATGGCAGTTCATTGCATGAATTTTAAAAG | 16 |
|   | CACAGCTGATCTCTGCCTTCTCTGTAATAGAC | 24 |
|   | CAGAACAAGAAATACAATTC | 18 |

As alluded to above, primers included in the primer/probe sets can be used to prime synthesis of copies of an HIV 1 target sequence in the case of SEQ ID NOs. 2, 3, 5, 6, 8, 9, 12, and 13; and copies of an HIV 2 target sequence in the case of SEQ ID NOs. 16, 17, 19, 20, 23 and 24. The remaining SEQ ID NOs. (SEQ ID NOs. 4, 7, 10, 11, 14, 18, 21, and 22), hybridize with the amplification products of either or both of the primer sequences found in the same primer/probe set. For example, primer/probe set 6 is specific for HIV 2 insofar as SEQ. ID. NOs. 19 and 20 prime synthesis of the HIV 2 target sequence and SEQ. ID. NOs. 21 and 22 hybridize with the amplification products produced by SEQ. ID. NOs. 19 and 20. Hence, the probe sequences are also specific for the various subtypes of HIV 1 or HIV 2.

Primer sequences generally comprise deoxyribonucleic acid (DNA), or ribonucleic acid (RNA). Probe sequences on the other hand may comprise DNA, RNA or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. patent applications Nos. 5,464,746; 5,424,414; and 4,948,882 all of which are herein incorporated by reference.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The term "test sample" as used herein, means anything suspected of containing an HIV target sequence. The test sample is or can be derived from any biological source, such as for example, blood, ocular lens fluid, cerebral spinal fluid, milk, ascites fluid, synovial fluid, peritoneal fluid, amniotic fluid, tissue, fermentation broths, cell cultures and the like. The test sample can be used (i) directly as obtained from the source or (ii) following a pre-treatment to modify the character of the sample. Thus, the test sample can be pretreated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

A "target sequence" as used herein means a nucleic acid sequence that is detected, amplified, or both amplified and detected using the primer/probe sets herein provided. Additionally, while the term target sequence is sometimes referred to as single stranded, those skilled in the art will recognize that the target sequence may actually be double stranded. Thus, in cases where the target is double stranded, primer sequences of the present invention will amplify both strands of the target sequence.

As mentioned earlier, the primer sequences of any particular primer/probe set (by themselves or with additional oligonucleotides) can be used as amplification primers according to nucleic acid amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930 all of which are herein incorporated by reference. Generically, these exemplified amplification reactions generate multiple copies of a DNA target sequence.

In accordance with the present invention, the target sequence may indeed be DNA, on the other hand in light of the RNA nature of the HIV genome, the primer/probe sets may be employed according to an "RT PCR" format which is described in U.S. Pat. Nos. 5,322,770 and 5,310,652 both of which are herein incorporated by reference. Briefly, the RT PCR format provides a method of transcribing a strand of DNA from an RNA target sequence. The copied DNA strand transcribed from the RNA target is commonly referred to as "cDNA" which then can serve as a template for amplification by any of the methods mentioned above. The process of generating cDNA shares many of the hybridization and extension principles surrounding other amplification methods such as PCR, but the enzyme employed should have reverse transcriptase activity. Enzymes having reverse transcriptase activity, as well as the RT PCR process, are well known and therefore don't warrant further discussion. Additionally, other methods for synthesizing cDNA are also known and include commonly owned U.S. patent application Ser. No. 08/356,287 filed Feb. 22, 1995, which is herein incorporated by reference.

According to a preferred embodiment, the primer/probe sets are employed in the "oligonucleotide hybridization PCR" (variably referred to herein as "OH PCR") amplification reaction as described in U.S. patent application Ser. No. 08/514,704, filed Aug. 14, 1995, that is herein incorporated by reference. Briefly, the reagents employed in the preferred method comprise at least one primer/probe set (designated herein as primer/probe sets 1–8), as well as other reagents for performing an amplification reaction. "Other reagents for performing an amplification reaction" or "nucleic acid amplification reagents" include reagents which are well known and may include, but are not limited to, an enzyme having polymerase activity, enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

The preferred method generally comprises the steps of (a) forming a reaction mixture comprising nucleic acid amplification reagents, at least one primer/probe set of the present invention, and a test sample suspected of containing a target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of the target sequence (HIV) in the sample. It will be understood that step (b) of the above method can be repeated several times prior to step (c) by thermal cycling the reaction mixture between 10 and 100 times, more typically between 20 and 60 times, as is well known in the art.

Amplification conditions are defined generally as conditions which promote annealing and extension of one or more nucleic acid sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer/probe set is well within ordinary skill of one practicing this art.

According to the OH PCR method, it is preferable to select primers, probes and reaction conditions such that the probe sequence has a lower melt temperature than the primer sequences so that upon placing the reaction mixture under amplification conditions copies of the target sequence or its complement (variably referred to as an amplicon) are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid for example between about 8 minutes to about 15 minutes, preferably less than 2 minutes. Such a rapid cooling favors hybrid formation between the copies of the target sequence and the probe rather than, for example, hybrid formation between complementary strands of the amplicon.

In cases where labels are employed to detect primer sequence products, primer sequences are labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

Upon formation of the copy sequence/probe hybrids, the differential labels (i.e. capture and detection labels) on the copy sequence and probe sequence can be used to separate and detect such hybrids. Preferably, detection is performed according to the protocols used by the commercially available Abbott LCx® instrumentation (Abbott Laboratories; Abbott Park, Ill.).

As previously discussed, the target sequence may be DNA or the target sequence may be imbedded within the HIV genome and therefore the target sequence may be in the form of RNA. In cases where the target sequence is part of the HIV genome, it is preferable to include an enzyme having reverse transcriptase activity as part of the so-called nucleic acid amplification reagents to enable production of cDNA for subsequent amplification. According to this embodiment, the primer sequences also serve as primers for cDNA synthesis. Although the invention contemplates distinct steps of cDNA production and then amplification and detection of amplified cDNA sequences, it will be understood that these processes may take place simultaneously in a single amplification reaction mixture.

According to another embodiment, HIV 1 and HIV 2 can be detected simultaneously in a single reaction using a combination of two primer/probe sets (i.e. one selected from the HIV 1 specific primer/probe sets and the other selected from the HIV 2 specific primer/probe sets). For example, a test sample could be contacted with primer/probe sets 1 and 8 along with amplification reagents, which may or may not include an enzyme having reverse transcriptase activity, to amplify and detect the presence of HIV 1 and HIV 2 in a test sample.

The oligonucleotides of the present invention also can be provided as part of a kit useful for detecting HIV 1 or HIV 2. The kits comprise one or more suitable containers containing one or more primer/probe sets according to the present invention, an enzyme having polymerase activity, deoxynucleotide triphosphates and, optionally, an enzyme having reverse transcriptase activity. Typically, at least one sequence bears a label, but detection is possible without this.

The following examples are provided to further illustrate the present invention and not intended to limit the invention.

EXAMPLES

The following examples demonstrate detection of various subtypes of HIV-1 and HIV-2 using the primer/probe sets herein provided. These DNA primers and probes comprising the primer/probe sets are identified as SEQUENCE ID NO.2, SEQUENCE ID NO.3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9, SEQUENCE ID NO. 10, SEQUENCE ID NO. 11, SEQUENCE ID NO. 12, SEQUENCE ID NO. 13, SEQUENCE ID NO. 14, SEQUENCE ID NO. 16, SEQUENCE ID NO. 17, SEQUENCE ID NO. 18, SEQUENCE ID NO. 19, SEQUENCE ID NO. 20, SEQUENCE ID NO. 21, SEQUENCE ID NO. 22, SEQUENCE ID NO. 23 and SEQUENCE ID NO. 24. SEQUENCE ID NO. 2, SEQUENCE ID NO. 3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9, SEQUENCE ID NO. 10, SEQUENCE ID NO. 11, SEQUENCE ID NO. 12, SEQUENCE ID NO. 13 and SEQUENCE ID NO. 14 are specific for HIV-1. A representative target sequence from HIV-1 (subtype B, strain MN) is designated herein as SEQ ID NO. 1. SEQUENCE ID NO. 16, SEQUENCE ID NO. 17, SEQUENCE ID NO. 18, SEQUENCE ID NO. 19, SEQUENCE ID NO. 20, SEQUENCE ID NO. 21, SEQUENCE ID NO. 22, SEQUENCE ID NO. 23 and SEQUENCE ID NO. 24 are specific for HIV-2. A representative target sequence from HIV-2 (subtype A, strain NIH-Z) is designated herein as SEQ ID NO. 15. All primers and probes are consensus sequences derived from 31 HIV-1 group M (subtypes A, B and D) and group O isolates and 14 HIV-2 isolates of both the A and B subtypes for the HIV-2 sequences.

In the following examples, SEQ ID NO. 2, SEQ ID NO. 3, SEQ ID NO. 5, SEQ ID NO. 6, SEQ ID NO. 8, SEQ ID NO. 9, SEQ ID NO. 12 and SEQ ID NO. 13 are used as consensus amplification primers specific for the HIV-1 target sequence. SEQ ID NO. 4, SEQ ID NO. 7, SEQ ID NO. 10, SEQ ID NO. 11 and SEQ ID NO. 14 are used as consensus internal hybridization probes for the HIV-1 amplification product. SEQ ID NO. 16, SEQ ID NO. 17, SEQ ID NO. 19, SEQ ID NO. 20, SEQ ID NO. 23 and SEQ ID NO. 24 are used as consensus amplification primers specific for the HIV-2 target sequence and SEQ ID NO. 18, SEQ ID NO. 21 and SEQ ID NO. 22 are used as consensus internal hybridization probes for the HIV-2 amplification product.

Example 1

Preparation of HIV Primers and Probes

A. HIV-1 and HIV-2 Consensus Primers. Consensus primers were designed to detect all known HIV-1 or HIV-2 subtypes by oligonucleotide hybridization PCR. These primers were SEQ ID NO. 2, SEQ ID NO. 3, SEQ ID NO. 5, SEQ ID NO. 6, SEQ ID NO. 8, SEQ ID NO. 9, SEQ ID NO. 12 and SEQ ID NO. 13 for HIV-1, and SEQ ID NO. 16, SEQ ID NO. 17, SEQ ID NO. 19, SEQ ID NO. 20, SEQ ID NO. 23 and SEQ ID NO. 24 for HIV-2. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

B. HIV-1 and HIV-2 Consensus Probes. Consensus probes were designed to hybridize with the amplified HIV target sequence by oligonucleotide hybridization. These probes were SEQ ID NO. 4, SEQ ID NO. 7, SEQ ID NO. 10, SEQ ID NO. 11 and SEQ ID NO. 14 for HIV-1, and SEQ ID NO. 18, SEQ ID NO. 21 and SEQ ID NO. 22 for HIV-2. Probe sequences were synthesized using standard oligonucleotide synthesis methodology and haptenated with 2 carbazoles at the 5' end using standard cyanoethyl phosphoramidite coupling chemistry as described in U.S. Pat. No. 5,464,746 (herein incorporated by reference), and blocked with phosphate at the 3' end.

Example 2

Sensitivity of HIV-1 Detection

HIV-1, subtype B has been reported as the most common strain of HIV-1 found in Europe and the United States, so it was used to assess the sensitivity of the different HIV-1 consensus primer/probe sets. RNA was isolated from gradient purified HIV-1, subtype B virions (HIV-1$_{MN}$, Advanced Biotechnologies Inc., Columbia, Md.) using the Qiagen RNA extraction procedure and column methodology as described by the manufacturer (Qiagen, Frankfurt, Germany). RNA was quantitated in viral RNA copies per milliliter and diluted into 1 ng/$\mu$l ribosomal RNA to levels appropriate for detection.

Four different HIV-1 consensus primer/probe sets were evaluated: set #1 used SEQ ID NOs. 2 and 3 as primers and SEQ ID NO. 4 as probe, set #2 used SEQ ID NOs. 5 and 6 as primers and SEQ ID NO. 7 as probe, set #3 used SEQ ID NOs. 8 and 9 as primers and SEQ ID NOs. 10 and 11 as probes, and set #4 used SEQ ID NOs. 12 and 13 as primers and SEQ ID NO. 14 as probe. All sequences were prepared as described in Example 1.

Dilutions of the purified HIV-1 RNA were reverse transcribed, PCR amplified and detected using the four HIV-1 consensus primer/probe sets in separate reactions. RT-PCR was performed using 50 mM Bicine, pH 8.25, 115 mM potassium acetate, 0.5 mM EDTA, 8% glycerol, 10 μg/ml bovine serum albumin (BSA) and 0.02% sodium azide. Recombinant *Thermus thermophilus* polymerase was used at a concentration of 5 units/reaction, with dNTPs (dATP, dGTP, dTTP and dCTP) present at a final concentration of 0.15 mM each. Primers were used at a concentration of 500 nM each, and probes at a concentration of 10 nM each. A final concentration of 2.5 mM $MnCl_2$ was used in a total reaction volume of 0.2 ml, with sample volume of 25 to 50 μl. The negative control was composed of 100 ng of ribosomal RNA/reaction.

Reaction mixtures were reverse transcribed and amplified in a Perkin-Elmer 480 Thermal Cycler. Reaction mixtures were first incubated at 62° C. for 30 minutes to reverse transcribe the RNA, followed by 30 seconds at 94° C. PCR amplification was then initiated through a touchdown or step-down protocol to aid in the stringency of the reaction in the early stages of amplification. This utilized 8 cycles as follows: 1 cycle at 70° C. for 80 seconds then 94° C. for 30 seconds followed by 1 cycle of 69° C. for 80 seconds then 94° C. for 30 seconds, followed by 1 cycle of 68° C. for 80 seconds then 94° C. for 30 seconds, followed by 1 cycle of 67° C. for 80 seconds then 94° C. for 30 seconds, followed by 1 cycle of 66° C. for 80 seconds then 94° C. for 30 seconds, followed by 1 cycle of 65° C. for 80 seconds then 94° C. for 30 seconds, followed by 1 cycle of 64° C. for 80 seconds then 94° C. for 30 seconds, followed by 1 cycle of 63° C. for 80 seconds then 94° C. for 30 seconds. Further amplification was then accomplished with 35 cycles with each cycle being 62° C. for 80 seconds then 94° C. for 30 seconds. After the reaction mixtures were thermal cycled, the mixtures were maintained at 97° C. for 15 minutes and probe oligo hybridization was accomplished by lowering the temperature to 4° C. within 2 minutes. Samples were held at 4° C. until detection of reaction products.

Reaction products were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The enzyme substrate used was methylumbelliferyl phosphate (MUP), with the rate of conversion of MUP to MU (methyl-umbelliferone) measured and reported as counts/second/second (c/s/s).

Data from this experiment is presented in TABLE 3 and shows detection of HIV-1, subtype B at concentrations as low as 10 molecules/assay (mol/assay) using HIV-1 primer/probe sets 1, 2 and 3, and detection of 100 molecules/assay using HIV-1 primer/probe set 4.

TABLE 3

| [HIV-1] mol/assay | Set #1 LCx ® rate | Set #2 LCx ® rate | Set #3 LCx ® rate | Set #4 LCx ® rate |
| --- | --- | --- | --- | --- |
| 10,000 | 2485.4 | 1389.6 | 1179.6 | 1459.3 |
| 1000 | 2323.8 | 1370.4 | 1061.1 | 892.6 |

TABLE 3-continued

| [HIV-1] mol/assay | Set #1 LCx ® rate | Set #2 LCx ® rate | Set #3 LCx ® rate | Set #4 LCx ® rate |
| --- | --- | --- | --- | --- |
| 100 | 1452.7 | 1358.2 | 605.2 | 211.9 |
| 10 | 490.0 | 835.3 | 440.6 | 73.8 |
| 0 | 33.0 | 18.7 | 48.1 | 59.7 |

Example 3

Sensitivity of HIV-2 Detection

HIV-2, subtype A, was used to assess the sensitivity of the different HIV-2 consensus primer/probe sets. RNA was isolated from gradient purified HIV-2, subtype A virions (HIV-2$_{NIHZ}$, Advanced Biotechnologies Inc., Columbia, Md.) using the Qiagen RNA extraction procedure and column methodology as described by the manufacturer (Qiagen, Frankfurt, Germany). RNA was purified from virions that were initially quantitated by electron microscopy. The resulting purified RNA was diluted into 1 ng/μl ribosomal RNA to levels appropriate for detection.

Three different HIV-2 consensus primer/probe sets were evaluated: set #5 used SEQ ID NOs. 16 and 17 as primers and SEQ ID NO. 18 as probe, set #6 used SEQ ID NOs. 19 and 20 as primers and SEQ ID NO.22 as probe (although SEQ ID NO 21 could also have been employed as a probe alone or in combination with SEQ ID NO. 22), and set #7 used SEQ ID NOs. 20 and 23 as primers and SEQ ID NO. 21 as probe. All sequences were prepared as described in Example 1.

Reaction mixtures were prepared, reverse transcribed, amplified and detected using the three HIV-2 consensus primer/probe sets in separate reactions, as described in Example 2.

Results presented in TABLE 4 show detection of HIV-2 to concentrations as low as 1 molecule/assay using HIV-2 consensus primer/probe sets 5 and 6, and detection of 100 molecules/assay using HIV-2 primer/probe set 7.

TABLE 4

| [HIV-2] mol/assay | Set #5 LCx ® rate | Set #6 LCx ® rate | Set #7 LCx ® rate |
| --- | --- | --- | --- |
| 10,000 | 2254.3 | 1427.3 | 501.1 |
| 1000 | 2310.5 | 1309.6 | 541.2 |
| 100 | 2290.6 | 1084.9 | 343.6 |
| 10 | 1967.5 | 750.3 | 75.1 |
| 1 | 1116.9 | 371.4 | 49.0 |
| 0 | 28.4 | 78.6 | 48.1 |

Example 4

HIV-1 Subtype Detection

The genetic divergence of HIV is the most challenging aspect to detection. There is a need for assays that accurately detect all subtypes, including the most widely divergent "O" subtype. Serum samples were obtained from Digene (Silver Spring, Md.) of HIV-1 subtypes A through F, and two isolates of HIV-1, subtype O. Viral RNA was extracted and purified from each isolate using Qiagen columns and methodology as described by the manufacturer (Qiagen, Frankfurt, Germany). RNA was quantitated in viral RNA copies per milliliter and ten-fold serial dilutions were made into 1 ng/μl ribosomal RNA for detection. Table 5 shows the amount of RNA (molecules/assay) used per reaction at each sample dilution for each subtype.

TABLE 5

| HIV-1 Subtype | RNA molecules/assay Sample Dilution | | | | |
|---|---|---|---|---|---|
| | $10^{-1}$ | $10^{-2}$ | $10^{-3}$ | $10^{-4}$ | $10^{-5}$ |
| A | 1737 | 173 | 17.3 | 1.73 | 0.17 |
| B | 890 | 89 | 8.9 | 0.89 | 0.09 |
| C | 247 | 24.7 | 2.47 | 0.25 | 0.03 |
| D | 20,700 | 2070 | 207 | 20.7 | 2.07 |
| E | 7170 | 717 | 71.7 | 7.17 | 0.72 |
| F | 24,000 | 2400 | 240 | 24 | 2.4 |
| HAM O | 66,460 | 6646 | 664.6 | 66.46 | 6.65 |
| LA O | 149,000 | 14,900 | 1490 | 149 | 14.9 |

The four different HIV-1 consensus primer/probe sets were used in separate reactions to reverse transcribe, amplify and detect the sample RNA from the various HIV-1 subtypes as described in Example 2. Subtype O was only tested with HIV-1 primer/probe set #1. Tables 6 through 9 below show the results of this testing.

TABLE 6

| HIV-1 Subtype | HIV-1 Set #1 LCx ® rate (c/s/s) Sample Dilution | | | | |
|---|---|---|---|---|---|
| | $10^{-1}$ | $10^{-2}$ | $10^{-3}$ | $10^{-4}$ | $10^{-5}$ |
| A | 1995 | 1530 | 559 | 45 | 37 |
| B | 2103 | 1979 | 750 | 31 | 27 |
| C | 740 | 135 | 133 | 26 | 24 |
| D | 1988 | 2042 | 1907 | 1226 | 528 |
| E | 2040 | 1954 | 1584 | 661 | 71 |
| F | 2027 | 1967 | 1871 | 1116 | 461 |
| HAM O | 1315 | 1389 | 1507 | 1224 | 168 |
| LA O | 1206 | 1413 | 1509 | 1403 | 650 |

HIV-1 primer/probe set #1 detected all HIV-1 subtypes tested in Table 6 above, including the widely divergent O subtypes, in a sensitivity range between 100 and 1 molecules/assay.

TABLE 7

| HIV-1 Subtype | HIV-1 Set #2 LCx ® rate (c/s/s) Sample Dilution | | | | |
|---|---|---|---|---|---|
| | $10^{-1}$ | $10^{-2}$ | $10^{-3}$ | $10^{-4}$ | $10^{-5}$ |
| A | 1218 | 1207 | 791 | 165 | 34 |
| B | 1597 | 1873 | 1544 | 380 | 20 |
| C | 569 | 300 | * | * | * |
| D | 1864 | 1866 | 1796 | 1246 | 636 |
| E | 931 | 949 | 856 | 406 | 61 |
| F | 1872 | 1838 | 1882 | 1807 | 1063 |

HIV-1 primer/probe set #2 detected all HIV-1 subtypes tested in Table 7 above with a sensitivity similar to that of HIV-1 primer/probe set #1.

TABLE 8

| HIV-1 Subtype | HIV-1 Set #3 Sample Dilution | | | | |
|---|---|---|---|---|---|
| | $10^{-1}$ | $10^{-2}$ | $10^{-3}$ | $10^{-4}$ | $10^{-5}$ |
| A | + | + | − | − | − |
| B | + | − | − | − | − |
| C | − | − | − | − | − |
| D | ND | + | +/− | − | − |
| E | + | + | − | − | − |
| F | ND | + | + | + | − |

(ND = not determined)

HIV-1 primer/probe set #3 detected 5 of the 6 HIV-1 subtypes tested in Table 8 above with a sensitivity of approximately 200 mol/assay.

TABLE 9

| HIV-1 Subtype | HIV-1 Set #4 Sample Dilution | | | | |
|---|---|---|---|---|---|
| | $10^{-1}$ | $10^{-2}$ | $10^{-3}$ | $10^{-4}$ | $10^{-5}$ |
| A | − | − | − | − | − |
| B | + | − | − | − | − |
| C | − | − | − | − | ND |
| D | + | + | + | − | − |
| E | + | + | +/− | − | − |
| F | + | − | − | − | − |

(ND = not determined)

HIV-1 primer/probe set #4 detected 4 of the 6 HIV-1 subtypes tested in Table 9 above with a sensitivity of between 2000 to 200 mol/assay.

Example 5

Specificity of HIV-1 and HIV-2 Primer/Probe Sets

The specificity of HIV-1 primer/probe sets #1 and #2 was assessed against RNA which was extracted and purified from HIV-1 subtype B (strains MN and 3B) and HIV-2 serum samples as in Example 4. The two different HIV-1 consensus primer/probe sets were used in separate reactions to reverse transcribe, amplify and detect 1:10 dilutions of the sample RNA as described in Example 2. As shown in Table 10, both HIV-1 primer/probe sets detect both HIV-1 RNAs but do not detect RNA from the HIV-2 serum, indicating that the HIV-1 primer/probe sets are specific for HIV-1 detection and do not cross-react and detect HIV-2.

TABLE 10

| Sample RNA | HIV-1 Set #1 LCx ® rate | HIV-1 Set #2 LCx ® rate |
|---|---|---|
| HIV-1$_{MN}$ | 2317 | 1321 |
| HIV-1$_{3B}$ | 2366 | 1395 |
| HIV-2 | 109 | 19 |

Next, the specificity of HIV-2 primer/probe set #5 was assessed against RNA isolated from gradient purified HIV-1 as in Example 2. Dilutions of the purified HIV-1 RNA were reverse transcribed, PCR amplified and detected as in Example 2 using HIV-2 consensus primer/probe set #5, with HIV-1 consensus primer/probe set #1 used in separate reactions as a control. The results, shown in Table 11, indicate that HIV-2 primer/probe set #5 does not cross-react and detect HIV-1 RNA.

TABLE 11

| [HIV-1] mol/assay | HIV-1 Set #1 LCx ® rate | HIV-2 Set #5 LCx ® rate |
| --- | --- | --- |
| 1,000,000 | 1792 | 16 |
| 100,000 | 1819 | 15 |
| 10,000 | 1812 | 16 |
| 1000 | 1823 | 15 |
| 100 | 1714 | 15 |
| 10 | 517 | 15 |
| 0 | 27 | 16 |

Example 6

Detection of HIV-1 or HIV-2 with HIV-1 and HIV-2 Primer/Probes

In order to allow both HIV-1 and HIV-2 to be tested in one reaction instead of in two separate reactions, primer/probe sets for HIV-1 and HIV-2 would have to be used in the same reaction. The feasibility of this was tested by mixing primer/probe sets for HIV-1 and HIV-2 and using them to detect either HIV-1 or HIV-2 purified RNA.

HIV-1 and HIV-2 RNA were purified and quantitated as in Examples 2 and 3 respectively. The HIV-1 primer/probe set #1 and HIV-2 primer/probe set #8, which consisted of SEQ ID NOs. 16 and 24 as primers and SEQ ID NO. 18 as probe, prepared as described in Example 1, were used either together or separately to reverse transcribe, amplify and detect the dilutions of purified HIV-1 and HIV-2 RNA as described in Example 2. Results are shown in Table 12.

TABLE 12

| [HIV-1] mol/assay | HIV-1 LCx ® rate | HIV-1/2 LCx ® rate | [HIV-2] mol/assay | HIV-2 LCx ® rate | HIV-1/2 LCx ® rate |
| --- | --- | --- | --- | --- | --- |
| 10,000 | 2114.5 | 1858.3 | 10,000 | 2094.1 | 2261.6 |
| 1000 | 1708.0 | 1550.2 | 1000 | 2209.2 | 1966.8 |
| 100 | 680.8 | 539.6 | 100 | 2216.2 | 1066.6 |
| 10 | 112.6 | 151.0 | 10 | 1879.8 | 254.9 |
| 1 | ND | ND | 1 | 805 | 66.8 |
| 0 | 50.4 | 74.5 | 0 | 31 | 90.4 |

(ND = not determined)

While there was a 1.0 to 1.5 log decrease in detection of HIV-2 when the HIV-1 and HIV-2 primer/probe sets were used in the same reaction mixture, the sensitivity remained acceptable at approximately 10 molecules per reaction. Importantly, detection of HIV-1 was not altered by the inclusion of the HIV-2 primer/probe set with the HIV-1 primer/probe set in the HIV-1 reaction mixtures, with sensitivity remaining at approximately 10 molecules per reaction.

While the invention has been described in detail and with reference to specific embodiments, it will be apparent to one skilled in the art that various changes and modifications may be made to such embodiments without departing from the spirit and scope of the invention.

What is claimed is:

1. A primer/probe set for detecting HIV 1 or HIV 2 selected from the primer/probe sets consisting of: primer/probe set 1 (SEQ ID NOs 2, 3 and 4); primer/probe set 2 (SEQ ID NOs 5, 6 and 7); primer/probe set 3 (SEQ ID NOs 8, 9, 10 and 11); primer/probe set 4 (SEQ ID NOs 12, 13 and 14); primer/probe set 5 (SEQ ID NOs 16, 17 and 18); primer/probe set 6 (SEQ ID NOs 19, 20 and 21 or 22); primer/probe set 7 (SEQ ID NOs 23, 20 and 21); and primer/probe set 8 (SEQ ID NOs 16, 24 and 18).

2. A method of detecting HIV in a test sample, said method comprises the steps of:
   (a) forming a reaction mixture comprising nucleic acid amplification reagents, at least one primer/probe set of claim 1, and a test sample containing an HIV target sequence;
   (b) subjecting the mixture to amplification conditions to generate at least one copy of a nucleic acid sequence complementary to the target sequence;
   (c) hybridizing the probe to the nucleic acid sequence complementary to the target sequence, so as to form a hybrid comprising the probe and the nucleic acid sequence complementary to the target sequence; and
   (d) detecting the hybrid as an indication of the presence of HIV in the test sample.

3. The method of claim 2 wherein said amplification reagents include an enzyme having reverse transcriptase activity and said method further comprises the step, after step (a) and prior to step (b), of forming a cDNA from an HIV genome.

4. The method of claim 2 wherein said at least one primer/probe set is selected from the primer/probe sets consisting of: primer/probe set 1 (SEQ ID NOs 2, 3 and 4); primer/probe set 2 (SEQ ID NOs 5, 6 and 7) primer/probe set 3 (SEQ ID NOs 8, 9, 10 and 11); and primer/probe set 4 (SEQ ID NOs 12, 13 and 14).

5. The method of claim 2 wherein said at least one primer/probe set is selected from the primer/probes sets consisting of: primer/probe set 5 (SEQ ID NOs 16, 17 and 18); primer/probe set 6 (SEQ ID NOs 19, 20 and 21 or 22); primer/probe set 7 (SEQ ID NOs 23, 20 and 21); and primer/probe set 8 (SEQ ID NOs 16, 24 and 18).

6. The method of claim 2 wherein step (b) is repeated between 10 and 100 times.

7. A kit comprising:
   a) at least one primer/probe set selected from the group consisting of: primer/probe set 1 (SEQ ID NOs 2, 3 and 4), primer/probe set 2 (SEQ ID NOs 5, 6 and 7), primer/probe set 3 (SEQ ID NOs 8, 9, 10 and 11), primer/probe set 4 (SEQ ID NOs 12, 13 and 14), primer/probe set 5 (SEQ ID NOs 16, 17 and 18), primer/probe set 6 (SEQ ID NOs 19, 20 and 21 or 22), primer/probe set 7 (SEQ ID NOs 23, 20 and 21), and primer/probe set 8 (SEQ ID NOs 16, 24 and 18); and
   b) amplification reagents.

8. The kit of claim 7 wherein said amplification reagents comprise an enzyme having reverse transcriptase activity.

9. The kit of claim 7 wherein said kit comprises at least two primer/probe sets wherein
(a) one of the at least two primer/probe sets is selected from the group consisting of primer/probe set 1 (SEQ ID NOs 2, 3 and 4), primer/probe set 2 (SEQ ID NOs 5, 6 and 7), primer/probe set 3 (SEQ ID NOs 8, 9,10 and 11), primer/probe set 4 (SEQ ID NOs 12, 13 and 14); and
(b) one of the at least two primer/probe sets is selected from the group consisting of primer/probe set 5 (SEQ ID NOs 16, 17 and 18), primer/probe set 6 (SEQ ID NOs 19, 20, 21 and 22), primer/probe set 7 (SEQ ID NOs 23, 20, 21 and 22), and primer/probe set 8 (SEQ ID NOs 16, 24 and 18).

* * * * *